United States Patent [19]

Horn

[11] Patent Number: 4,657,925
[45] Date of Patent: * Apr. 14, 1987

[54] METHOD AND COMPOSITIONS FOR REDUCING THE INTRAOCULAR PRESSURE OF MAMMALS

[75] Inventor: Alan S. Horn, Noordhorn, Netherlands

[73] Assignee: Nelson Research & Development Co., Irvine, Calif.

[*] Notice: The portion of the term of this patent subsequent to Jan. 14, 2003 has been disclaimed.

[21] Appl. No.: 811,768

[22] Filed: Dec. 20, 1985

Related U.S. Application Data

[63] Continuation-in-part of Ser. No. 640,685, Aug. 13, 1984, Pat. No. 4,564,628.

[51] Int. Cl.[4] .................... A61K 31/38; A61K 31/40; A61K 31/34; C07D 333/12
[52] U.S. Cl. .................... 514/438; 514/357; 514/399; 514/415; 514/427; 514/471; 514/521; 514/523; 549/75
[58] Field of Search ............... 514/438, 357, 415, 427, 514/399, 471, 521, 523; 549/75

[56] References Cited

U.S. PATENT DOCUMENTS

| | | |
|---|---|---|
| 3,930,022 | 12/1975 | Hauck et al. |
| 4,076,843 | 2/1978 | Hauck et al. |
| 4,267,373 | 5/1981 | Hauck et al. |
| 4,314,082 | 2/1982 | Stout |
| 4,410,519 | 10/1983 | Seiler et al. |
| 4,564,628 | 1/1986 | Horn .................... 514/438 |

FOREIGN PATENT DOCUMENTS

| | | |
|---|---|---|
| 64964 | 6/1982 | European Pat. Off. |
| 1597140 | 9/1981 | United Kingdom |

OTHER PUBLICATIONS

McDermed et al., Journal of Medicinal Chemistry, 1975, vol. 18, No. 4, pp. 362-367.
Hacksell et al., Journal of Medicinal Chemistry, vol. 22, No. 12 at pp. 1469-1475.
Beaulieu et al., European Journal of Pharmacology, 105 (1984) at pp. 15-21.

*Primary Examiner*—Alan Siegel
*Attorney, Agent, or Firm*—Robert J. Baran

[57] ABSTRACT

This invention provides a method for reducing the intraocular pressure in mammals which comprises administering an effective amount of a compound selected from the group consisting of compounds represented by the general formula:

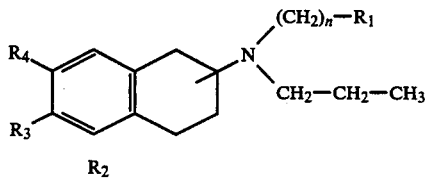

where $R_2$, $R_3$ and $R_4$ are each selected from the group consisting of H, and OA; A is H or

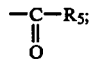

$R_5$ is selected from the group consisting of alkyl and aromatic residues; n is 2 or 3; and $R_1$ is selected from the group consisting of 3-hydroxyphenyl, 4-hydroxyphenyl, 3-pyridyl, 4-pyridyl,

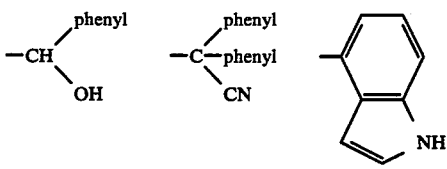

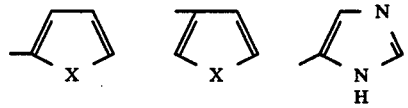

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof. This invention further provides compositions useful in such method of reducing the intraocular pressure in mammals.

19 Claims, No Drawings

METHOD AND COMPOSITIONS FOR REDUCING THE INTRAOCULAR PRESSURE OF MAMMALS

CROSS REFERENCE TO RELATED APPLICATIONS

This patent application is a continuation in part of U.S. patent application Ser. No. 640,685, filed on Aug. 13, 1984, now U.S. Pat. No. 4,564,628, in the name of Alan S. Horn.

BACKGROUND OF THE INVENTION

1. Field of the Invetion

This invention relates to methods of treating mammals to lower intraocular pressure and thus is useful in alleviating glaucoma. This invention also provides compositions usefu in such method.

2. Background of the Art

Glaucoma is a disorder characterized by increased intraocular pressure that may cause impaired vision, ranging from slight loss to absolute blindness. It has been shown that certain compounds can lower intraocular pressure in various mammals. For example, it has been suggested that Bromocriptine may lower intraocular pressure in man. (See *The Lancet.*

Feb.4, 1984, "Bromocriptine Eyedrops Lower Intraocular Pressure without Affecting Prolactin Levels.", by Mekki, et al. at pages 287–288.)

Similarly, Bromocriptine, as well as lergotrile and pergolide has been shown to lower the intraocular pressure of rabbit and the latter two compounds also lowered the intraocular pressure of monkeys. (See Potter, D. E. and Burke, J. A. (1982/1983). Effects of Ergoline Derivatives on Intraocular Pressure and Iris Function in Rabbits and Monkeys. Curr. Eye Res. 2, 281–288 and Potter, D. E., Burke, J. A. and Chang, F. W. (1984). Ocular Hypotensive Action of Ergoline Derivatives in Rabbits: Effects of Sympathectomy and Domperidone Pretreatment. Curr. Eye Res. 3, 307–314.)

It has also been shown that certain dopamine analogs of the phenylethylamine class, i.e. N-methyldopamine, N,N-dimethyl-dopamine and N,N-di-n-propyldopamine, may alter ocular function by operating through a variety of mechanisms. However, N-methyl dopamine appeared to function by suppressing aqueous humor formation. (See Potter, D. E., Burke, J. A. and Chang, F. W. (1984). Alteration in Ocular Function Induced by Phenylethylamine Analogs of Dopamine. Curr. Eye Res. 3, 851–859.)

Finally, certain aminotetralins were shown to lower intraocular pressure in rabbits. (See Burke, J. A. Chang, F. L. and Potter, D. E. (1984) Effects of Aminotetralins on Intraocular Pressure and Pupillary Function in Rabbits. J. Auton. Pharmacol. 4, 185–192.)

Thus, it is clear that many compounds have been suggested for lowering the intraocular pressure in mammals and research continues to find even more potent compounds for the treatment of glaucoma.

SUMMARY OF THE INVENTION

This invention provides compositions useful in lowering the intraocular pressure of mammals, e.g. humans, which comprise a intraocular pressure-lowering amount of a compound selected from the group of compounds represented by the general formula:

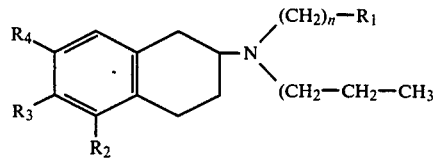

where $R_2$, $R_3$ and $R_4$ are each selected from the group consisting of H, and OA; A is H or

$R_5$ is selected from the group consisting of alkyl and aromatic residues; n is 2 or 3; and $R_1$ is selected from the group consisting of 3-hydroxyphenyl, 4-hydroxyphenyl, 3-pyridyl, 4-pyridyl,

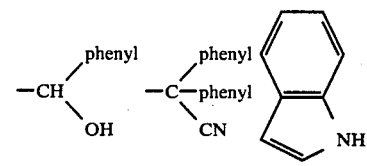

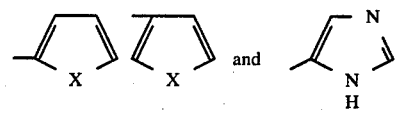

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof.

This invention further provides a method for reducing the intraocular pressure in mammals which comprises administering an effective amount of a compound selected from the group consisting of compounds represented by the general formula:

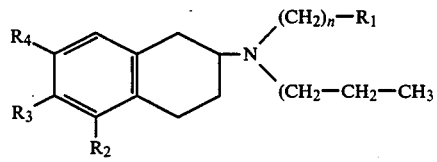

where $R_2$, $R_3$ and $R_4$ are each selected from the group consisting of H, and OA; A is H or

is selected from the group consisting of alkyl and aromatic residues; n is 2 or 3; and $R_1$ is selected from the group consisting of 3-hydroxyphenyl, 4-hydroxyphenyl, 3-pyridyl, 4-pyridyl,

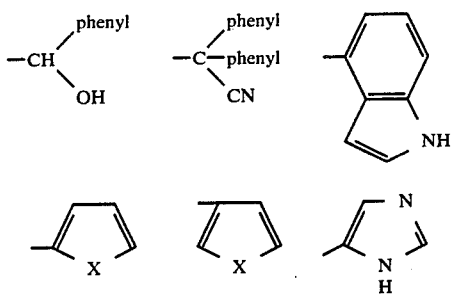

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof.

DETAILED DESCRIPTION OF THE INVENTION

The above compounds may be made by any of the methods disclosed in U.S. patent application Ser. No. 640,685, cited above, which is hereby incorporated by reference.

In a preferred embodiment of the instant invention $R_4$ is H and $R_2$ and $R_3$ are OH or $R_2$ is H and $R_3$ and $R_4$ are OH. That is, the catechol derivatives are one class of preferred compounds for the method and compositions of the present invention. In another preferred embodiment $R_3$ and $R_4$ are H and $R_2$ is OH or $R_2$ and $R_3$ are H and $R_4$ is OH.

The preferred value for n is 2. X is preferably S. That is, in one preferred embodiment of the present invention $R_1$ is a thienyl group, i.e.

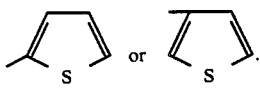

In a second preferred embodiment $R_1$ is selected from the group consisting of 3-pyridyl, 4-pyridyl

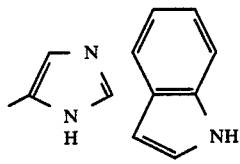

More preferably, $R_3$ and $R_4$ is H and $R_2$ is OH, n is 2 and X is S. That is, the N-thienylethyl substituted-2hydroxy N-propyl amino tetralins are more preferred for the method and compositions of the instant invention.

Even more preferably the method of the present invention comprises administering 2-(N-propyl-N-2-thienylethylamino)-5-hydroxytetralin to the eye of a mammal to reduce intraocular pressure. Moreover, the levo (−) isomer of this compound is believed to be the more active isomer for use in the method of the present invention.

Suitable ophthalmic carriers are known to those skilled in the art and all such conventional carriers may be employed in the present invention. Thus, a particular carrier may take the form of a sterile ophthalmic ointment, cream, gel, solution, or dispersion and preferably a solution. Also including as suitable ophthalmic carriers are slow releasing polymers, e.g. "Ocusert" polymers, "Hydron" polymers, etc. Stabilizers may also be used such as, for example, chelating agents, e.g. EDTA. Anti-oxidants may also be used, e.g. sodium bisulfite, sodium thiosulfite, 8-hydroxy quinoline or ascorbic acid. Sterility typically will be maintained by conventional ophthalmic preservatives, e.g. chlorbutanol, benzalkonium chloride, cetylpyridinium chloride, phenyl mercuric salts, thimerosal, phenethyl alcohol, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers or stabilizers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine, EDTA, sodium bisulfite and ascorbic acid.

The amount of active compound to be used in the therapeutic treatment of glaucoma will vary with the age of the patient and the severity of the glaucoma. Generally a dose level of one or two drops of the foregoing aqueous solution 1–4 times daily would be a suitable dosage amount. Generally, the concentration of active compound will vary between about 0.001 and about 5% and preferably between about 0.05 and about 1% (wt./v calculated on the basis of the free base) of said ophthalmic composition.

Preferably, the ophthalmic composition of this invention should have a pH within the range of about 4.0 to 9.0 when intended for topical application. Above and below this pH range the solution may irritate and sting the eye of the user. The solutions of the present invention may be maintained between about pH 4.0 and 7.5 with suitable amounts of buffering agents including borate, carbonate, phosphate. Tris (hydroxymethyl aminomethane), acetate and citrate buffers.

A preferred ophthalmic composition is a preserved aqueous solution containing the following ingredients at approximately the indicated concentration.

| | |
|---|---|
| Active compound | 0.001–1 wt. % |
| Stabilizer | 0.01–0.1 wt. % |
| Preservative | 0.005–0.5 wt. % |
| Buffer (sufficient to maintain pH between about 4.0 and 7.5) | 0.1–0.001 M |
| NaCl qs. ad. | (isotonic) |
| Water qs. ad. | 100% |

To illustrate the manner in which the invention may be carried out, the following examples are given. It is understood, however, that the example is for the purpose of illustration and the invention is not to be regarded as limited to any of the specific materials or conditions therein.

EXAMPLE 1

Male, albino New Zealand rabbits, female *Cebus apella* monkeys and cats of mixed sexes were used in this example. Rabbits were used primarily to screen for undue ocular toxicity of 2-(N-propyl-N-2-thienylethylamino)-5hydroxytetralin (active compound) before conducting experiments in monkeys. Cats were used to localize the site and mechanism of action of the active compound as either ganglionic, prejunctional or postjunctional.

A racemic mixture of 2-(N-propyl-N-2-thienylethylamino)-5-hydroxytetralin (active compound) was dissolved in distilled water (vehicle) on the day of the experiment. Solutions were administered in a masked manner, that is, solutions were prepareed by a person that was neither involved in drug administration nor measurement of intraocular pressure (IOP) and pupil diameter (PD). The solution of the active compound was applied unilaterally with the contralateral (fellow) eye receiving vehicle only. Five monkeys were treated bilaterally with vehicle; one to two vehicle-treated monkeys were included each time a different dose of the active compound was used. Doses of active compound tested were: 0.165, 0.5 and 1.65 mg.

Horizontal PD was measured utilizing an Optistick. After taking two baseline (0 time) measurements, aliquots (50μl) of the solution of the active compound and/or vehicle, only, were administered topically. Subsequently, IOP and PD measurements were made at 0.5, 1, 2, 3, 4 and 5 hours post drug. Additional readings were taken on subsequent days when it became apparent that the ocular effects of the active compound were protracted. Gross observations were made regarding signs of ocular irritation and systemic effects.

The active compound produced dose-related ocular hypotension, miosis and ptosis in monkeys at doses of 0.5 and 1.65 mg topically. Shortly after topical administration there was evidence of ocular irritation in the form of tearing, exudate and hyperemia. Subsequently, there was evidence of clouding of the cornea, miosis and ptosis. After the initial phase of exudation, the hyperemia, ptosis and miosis persisted for hours to days. At 144 hours and beyond, there were also signs of sympathetic suppression to extraocular (ptosis) and intraocular (miosis and hyperemia) structures.

The active compound also produced dose-related suppression of neuronally mediated contractions of the nictitans with minimal effects on contractions induced by norepinephrine intra-arterially (i.a.). This test is described in Potter, D. E. and Burke, J. A. (1984) An *In Vivo* Model for Discriminating $\alpha_2$- and $DA_2$- Adrenoceptor Activity in an Ocular Adnexa; Utility of the Cat Nictitating Membrane Preparation. Curr. Eye Res. 3, 1289–1298. The inhibitory effects of the active compound were fully reversible within 106 minutes after the last dose. Pretreatment with domperidone i.a. had no effect on contractions elicited by neuronal stimulation and by exogenous norepinephrine but produced a 100 fold shift in the inhibitory index of the active compound on neuronally mediated contractions of the nictitans.

These results demonstrate that the active compound, a $DA_2$ agonist, lowered IOP and produced miosis and ptosis in monkeys. The IOP and pupillary responses to the active compound responses occurred within several hours and, depending on the dose, persisted for many days. The acute response of the cat nictitans to the active compound i.a. was reversible and antagonized competitively by domperidone. These data would suggest that the acute phase of action is an action on $DA_2$ receptors in the periphery because the relatively selective antagonist, domperidone, penetrates the pial-glial barrier poorly. The chronic response to the active compound in monkeys would also appear to be due to suppression of sympathetic neuronal function and would appear to be slowly reversible. The prolonged phase of action is reminiscent of a guanethidine-or reserpine-like effect.

In summary, the active compound is a $DA_2$ agonist that lowers IOP in monkeys. Although it produces moderate ocular irritation at high doses, the compound provides a very prolonged ocular hypotensive action.

EXAMPLE 2

Racemic 2- (N-n-Propylamino) -5-methoxytetralin was resolved into its plus and minus optical isomers and then converted to (plus) and (minus) 2- (N-propyl-N-2-thienyl ethyl amino) -5-hydroxytetralin by the methods described in U.S. patent application Ser. No. 640,685 herein incorporated by reference.

The pharmacological activities of the plus and minus isomers was determined by examining their ability to displace the specific D-2 dopamine receptor binding of a tritium-containing racemic mixture of 2- (N-propyl-N-2thienylethyl amino) -5-hydroxytetralin to homogenates of calf brain corpus striatum. In this preparation, which is a modification of the one reported by Mulder et. al. "Kinetic and Pharmacological Profiles of the In-Vitro Binding of the Potent Dopamine Agonist $^3$H-N,N-dipropyl-2Aminotetralin to Rat Striatal Membranes," Eur. J. Pharmacol 112 (1985) 73–79, for rat brain corpus striatum, the tritium-containing racemic mixture had an affinity constant ($K_d$) of 1.6 nanomoles and a βmax of 26.0 picomoles/gm. The $IC_{50}$ values (i.e. the concentration of drug required to inhibit the binding of labelled drug by 50 percent for the minus and plus isomer were 0.5 and 71.0 nanomoles, respectively. Thus the levo (minus) isomer is 140 times more potent than the dextro (plus) isomer.

While particular embodiments of the invention have been described it will be understood of course that the invention is not limited thereto since many obvious modifications can be made and it is intended to include within this invention any such modifications as will fall within the scope of the appended claims.

Having now described the invention, I claim:

1. A method for reducing the intraocular pressure in mammals which comprises administering an effective amount of a compound selected from the group consisting of compounds represented by the general formula:

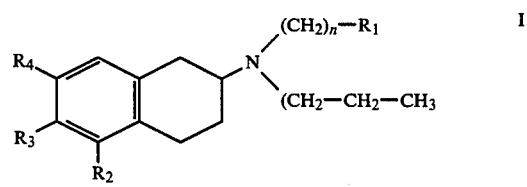

wherein $R_2$, $R_3$ and $R_4$ are each selected from the group consisting of H, and OA; A is H or

$R_5$ is selected from the group consisting of alkyl and aromatic residues; n is 2 or 3; and $R_1$ is selected from the group consisting of 3-pyridyl, 4-pyridyl,

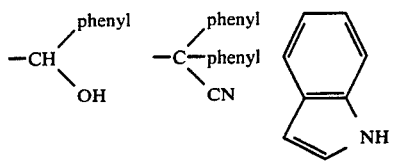
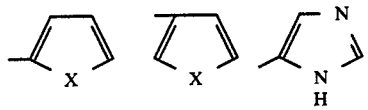

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof.

2. The method of claim 1 wherein $R_4$ is H and $R_2$ and $R_3$ are OH.

3. The method of claim 1, where $R_2$ is H and $R_3$ and $R_4$ are OH.

4. The method of claim 1, where $R_3$ and $R_4$ are H and $R_2$ is OH.

5. The method of claim 1, where $R_2$ and $R_3$ are H and $R_4$ is OH.

6. The method of claim 1, where n is 2.

7. The method of claim 1, where $R_1$ is a thienyl group.

8. The method of claim 1, where $R_1$ is selected from the group consisting of 3-pyridyl, 4-pyridyl,

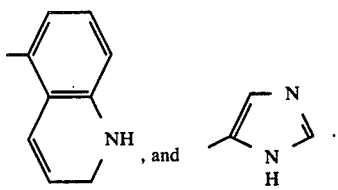

9. The method of claim 1 wherein said compound is 7-Hydroxy-2-(N-n-propyl-N-2-thienylethyl)-aminotetralin and pharmaceutically-acceptable salts thereof.

10. The method of claim 1 wherein said compound is 5-Hydroxy-2-(N-n-propyl-N-2-thienylethyl)-aminotetralin and pharmaceutically-acceptable salts thereof.

11. The method of claim 1 wherein said compound is 5-Hydroxy-2-(N-n-propyl-N-3-thienylethyl)-aminotetralin and pharmaceutically-acceptable salts thereof.

12. A composition for reducing the intraocular pressure in mammals which comprises an effective amount of a compound selected from the group consisting of compounds having the structural formula:

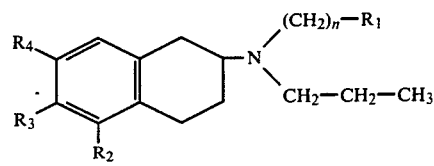

where $R_2$, $R_3$ and $R_4$ are each selected from the group consisting of H, and OA; A is H or

$R_5$ is selected from the group consisting of alkyl and aromatic residues; n is 2 or 3; and $R_1$ is selected from the group consisting of 3-pyridyl, 4-pyridyl,

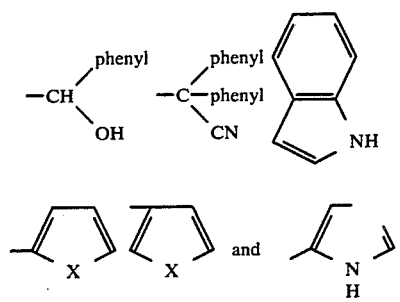

where X is S, O or NH, with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof, and an ophthalmic carrier.

13. The composition of claim 12 wherein said ophthalmic carrier is water.

14. The composition of claim 13, where $R_1$ is a thienyl group.

15. The composition of claim 13, where $R_1$ is selected from the group consisting of 3 pyridyl, 4 pyridyl,

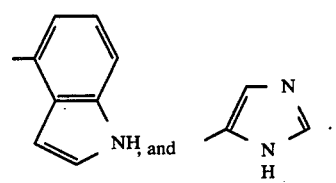

16. The composition of claim 13 wherein said compound is 7-Hydroxy-2-(N-n-propyl-N-2-thienylethyl)-aminotetralin and pharmaceutically-acceptable salts thereof.

17. The composition of claim 13 wherein said compound is 5-Hydroxy-2-(N-n-propyl-N-2-thienylethyl)-aminotetralin and pharmaceutically-acceptable salts thereof.

18. The composition of claim 13 wherein said compound is 5-Hydroxy-2-(N-n-propyl-N-3-thienylethyl)-aminotetralin and pharmaceutically-acceptable salts thereof.

19. The levo (minus) isomer of 2(N-propyl-N-2-thienylethyl-amino) -5-hydroxytetralin.

* * * * *